(12) United States Patent
Dunham et al.

(10) Patent No.: US 6,238,486 B1
(45) Date of Patent: May 29, 2001

(54) DETECTABLE CATIONIC FLOCCULANT AND METHOD OF USING SAME IN INDUSTRIAL FOOD PROCESSES

(75) Inventors: Andrew J. Dunham, DeKalb; Cathy C. Johnson, Geneva; Kristine S. Salmen, Naperville; John W. Sparapany, Bolingbrook; Anthony G. Sommese, Aurora, all of IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/266,058

(22) Filed: Mar. 10, 1999

(51) Int. Cl.[7] .............................. C13D 3/16; B01D 43/00; G01N 33/563; C08F 2/32

(52) U.S. Cl. ............................. 127/55; 127/53; 435/7.9; 435/7.92; 436/548; 526/207; 526/209; 526/210; 526/215; 526/220; 526/287; 526/292.2; 526/307

(58) Field of Search ................. 127/53, 55; 435/7.9, 435/7.92; 436/548; 526/207, 209, 210, 215, 220, 287, 292.2, 307

(56) References Cited

U.S. PATENT DOCUMENTS

| | | |
|---|---|---|
| 3,523,889 | 8/1970 | Eis . |
| 3,834,941 | 9/1974 | Schoenrock et al. . |
| 3,887,391 | 6/1975 | Schoenrock et al. . |
| 3,982,956 | 9/1976 | Schoenrock et al. . |
| 4,001,113 | 1/1977 | Schoenrock et al. . |
| 4,617,362 * | 10/1986 | Becker et al. ................ 526/209 |
| 4,990,259 | 2/1991 | Kearney et al. . |
| 5,051,487 * | 9/1991 | Bhattacharyya et al. ............ 526/287 |
| 5,102,553 | 4/1992 | Kearney et al. . |
| 5,338,541 * | 8/1994 | Matz et al. .............................. 424/71 |
| 5,429,952 | 7/1995 | Garner et al. . |
| 5,466,294 | 11/1995 | Kearney et al. . |
| 5,593,850 * | 1/1997 | Wetegrove et al. ................ 435/7.92 |
| 5,653,886 * | 8/1997 | Kerr et al. .......................... 210/727 |

FOREIGN PATENT DOCUMENTS

| | | |
|---|---|---|
| 1272191 | 7/1990 | (CA) . |
| 188 721 | 7/1986 | (EP) . |
| 535 347 | 4/1993 | (EP) . |
| 1244514 | 7/1995 | (IT) . |

OTHER PUBLICATIONS

"Environmental immunoassays: practical applications and recent developments", *Analusis*, 25 (7), M25–M29 (1997) no month provided.

* cited by examiner

*Primary Examiner*—David Brunsman
(74) *Attorney, Agent, or Firm*—Margaret M. Brumm; Thomas M. Breininger

(57) ABSTRACT

The invention provides novel cationic flocculant dispersion polymers that can be utilized in the methods disclosed herein. This invention also provides methods for detecting cationic flocculants wherein said flocculants may be made via a dispersion process, a latex process or a dry polymer process. The flocculants are used to flocculate solids from liquid components of an industrial food process. The detection method involves the use of monoclonal antibodies to determine the presence or concentration of the cationic flocculants in the liquids.

15 Claims, No Drawings

DETECTABLE CATIONIC FLOCCULANT AND METHOD OF USING SAME IN INDUSTRIAL FOOD PROCESSES

FIELD OF THE INVENTION

The present invention relates to compositions and methods for separating the solid component from a liquid-solid mixture of an industrial food process. More specifically, the present invention relates to compositions and methods for separating the solid component from a liquid-solid mixture present in an industrial food process, wherein it is desired to recover the liquid component of the industrial food process. More specifically, the present invention relates to a traceable high molecular weight cationic flocculant for use in flocculating a component of a stream in the manufacture of sugar, involving passing liquid through a filter medium, wherein the liquid present in said sugar process is further processed to recover additional sugar(s).

BACKGROUND OF THE INVENTION

In industrial food processes it is common that a solid-liquid mixture needs to be separated into its liquid component and its solid component. There are polymer flocculants available currently to perform this separation. However, useful materials in the liquid component of such separations are typically not harvested because of concern that the liquid component is contaminated with polymer flocculants. This concern about contamination has led to much valuable material being discarded.

For example, in the recovery of sugar, cationic flocculants are used to effect solid-liquid separation. The liquid portion still contains recoverable sugar, but this sugar is not recovered, because the liquid may have been contaminated with flocculant. In order not to waste this recoverable sugar, there is a recognized need to develop either an environmentally safe (for food use) polymer or a detectable polymer. Of these two routes, it was decided to pursue a detectable polymer as a solution.

In pursuing a solution it was noted that immunoassay detection technology was already in existence for the coagulant polymers epichlorohydrin dimethylamine (hereinafter "epi-DMA") and polydiallyldiammonium chloride (hereinafter "polyDADMAC"). Epi-DMA is available as Nalco®8105 from Nalco Chemical Company, One Nalco Center, Naperville, Ill. 60563 ((630) 305-1000). PolyDADMAC is available as Nalco®8103 from Nalco Chemical Company. Although these polymers are detectable, it was found that these polymers did not have a sufficient molecular weight to act as flocculants.

Building on the use of immunoassay as the detection method of choice, a 30/70 mole percent acrylamide/DADMAC copolymer (which is available from Nalco Chemical Company as Nalco®7527) was tested in the sugar application. This polymer has molecular weights greater than the coagulants, but not as high as a flocculant. Because of the high concentration of DADMAC, this polymer was detectable using the Nalco®8103 (polyDADMAC) immunoassay test kit. A field trial was run, which was a failure. Although detectable in the liquid component, the polymer did not form strong robust flocs and the solids were not effectively dewatered. This failure can be related to both charge and molecular weight. It was known that DADMAC monomer does not polymerize to high molecular weights, so copolymers containing DADMAC are more like coagulants than flocculants.

Based on the above results, the criteria for a polymer flocculant to be successful in this application were determined to be as follows:

1) polymer flocculant must form effective flocs that will effect solid-liquid separation (i.e. getting the correct charge),
2) the floc strength must be sufficient to withstand the shear of the dewatering process (i.e. having sufficient molecular weight), and
3) the polymer must be detectable (by immunoassay) to quantify the level of polymer in the liquid.

SUMMARY OF THE INVENTION

The first aspect of this invention is a cationic flocculant dispersion polymer comprising:

a first monomer component, which is nonionic;

a second monomer component, which is cationic; and a third monomer component which is diallyl dimethylammonium chloride;

wherein the first monomer component, which is nonionic, is selected from the group consisting of:

acrylamide, vinylacetate, vinylcaprolactam, protonated acrylamidopropylsulfonic acid, protonated 2-sulfoethylacrylate, substituted or non-substituted amides or esters of acrylic acid, including, but not limited to: N,N-dimethylacrylamide, N-t-butylacrylamide, N-isopropyl acrylamide, hydroxymethylacrylate, hydroxyethylacrylate, hydroxypropylacrylate, and hydroxybutylacrylate, substituted or non-substituted amides or esters of methacrylic acid, including, but not limited to: N,N-dimethylmethacrylamide, N-methylmethacrylamide, N-isopropyl methacrylamide, hydroxymethylmethacrylate, hydroxyethylmethacrylate, hydroxypropylmethacrylate, and hydroxybutylmethaciry-late;

wherein the second monomer component, which is cationic, is selected from the group consisting of: dimethylaminoethylacrylate methyl chloride salt (DMAEA.MCQ); dimethylaminoethylmethacrylate methyl chloride salt (DMAEM.MCQ); dimethylaminoethylmethacrylate methyl sulfate salt (DMAEM.MSQ); dimethylaminoethylmethacrylate benzyl chloride salt (DMAEM.BCQ); dimethylaminoethylacrylate methyl sulfate salt (DMAEA.MSQ); dimethylaminoethylacrylate benzyl chloride salt (DMAEA.BCQ), methacrylamidopropyl trimethylammonium chloride (MAPTAC); acrylamidopropyl trimethylammonium chloride (APTAC); 2-vinylpyridine; and 4-vinylpyridine.

The second aspect of this invention is a method of flocculating solids from the liquid component of an industrial food process, the method comprising the steps of:

a) adding a cationic flocculant polymer to a liquid component of an industrial food process which causes the formation of flocculated particles, wherein said cationic flocculant polymer comprises a first monomer component, which is nonionic;

a second monomer component, which is cationic; and a third monomer component which is diallyl dimethylammonium chloride;

wherein the first monomer component, which is nonionic, is selected from the group consisting of:

acrylamide, vinylacetate, vinylcaprolactam, protonated acrylamidopropylsulfonic acid, protonated 2-sulfoethylacrylate, substituted or non-substituted amides or esters of acrylic acid, including, but not limited to: N,N-dimethylacrylamide, N-t-butylacrylamide, N-isopropyl acrylamide, hydroxymethylacrylate, hydroxyethylacrylate, hydroxypropylacrylate, and hydroxybutylacrylate, substituted or non-substituted amides or esters of methacrylic acid, including, but not limited to: N,N-dimethylmethacrylamide, N-methylmethacrylamide, N-isopropyl methacrylamide, hydroxymethylmethacrylate, hydroxyethylmethacirylate, hydroxypropyhnethacrylate, and hydroxybutylmethacrylate;

wherein the second monomer component, which is cationic, is selected from the group consisting of: dimethylaminoethylacrylate methyl chloride salt (DMAEA.MCQ); dimethylaminoethylmethacrylate methyl chloride salt (DMAEM.MCQ); dimethylaminoethylmethacrylate methyl sulfate salt (DMAEM.MSQ); dimethylaminoethylmethacrylate benzyl chloride salt (DMAEM.BCQ); dimethylaminoethylacrylate methyl sulfate salt (DMAEA.MSQ); dimethylaminoethylacrylate benzyl chloride salt (DMAEA.BCQ), methacrylamidopropyl trimethylammonium chloride (MAPTAC); acrylamidopropyl trimethylammonium chloride (APTAC); 2-vinylpyridine; and 4-vinylpyridine;

b) separating said flocculated particles from said liquid component; and c) determining the concentration of said cationic flocculant polymer in the liquid; wherein the step of determining the concentration of the cationic flocculant polymer further comprises:

i) incubating the sample of liquid with a monoclonal antibody having an affinity for the cationic flocculant polymer, the affinity being strong enough to recognize a monomer antigen in the cationic flocculant polymer and to differentiate the cationic flocculant polymer from other polymers in the sample;

ii) detecting and measuring the degree of binding of the monoclonal antibody with the monomer antigen; and iii) determining the concentration of the cationic flocculant polymer based on the degree of binding of the monoclonal antibody.

DETAILED DESCRIPTION OF THE INVENTION

Throughout this patent application the following definitions apply:

Polymeric Dispersants—usually an anionic polymer with weight average molecular weights ranging from 1000 to 50,000 atomic mass units (hereinafter "amu"), but preferably the molecular weight is in the 3000–15,000 amu range. Dispersants, as the name implies are added to processes to keep suspended particles dispersed and stop them from forming deposits or scale. Dispersants work by introducing like charge to a charged species. This in turn creates repulsions that keep the charged particles suspended. Free radical polymerizations with acrylic based monomers or anhydrides (like maleic) are the most common way to make these polymers. Boilers and cooling towers are the main areas where dispersants are used.

Polymeric Coagulants—usually cationic, but can also be anionic. Weight average molecular weights can range from 10,000 to 1,000,000 amu, but are preferably in the range of 20,000–500,000 amu. Coagulants usually have a high charge density. Because of this high charge density, coagulants act as charge neutralizers when they interact with oppositely charged particles. There are two common methods to make coagulants, through free radical polymerization of acrylic or allylic-based monomers and addition polymerizations. Examples of free radical-based polymers include poly DADMAC and low molecular weight cationic acrylamides. Nalco®8103 is a polyDADMAC that can be detected by the immunoassay. Examples of addition polymers are epichlorohydrin-dimethylamine (epi-DMA) polymers and ethylene dichloride/ammonia polymers (hereinafter "EDC-ammonia"). Nalco®8105 is an epi-DMA coagulant that can be detected by a commercial available immunoassay kit.

Polymeric Flocculants—can be cationic, anionic or neutral in charge. Unlike coagulants that have very high charge densities, flocculants can have varying charge. Weight average molecular weights are extremely large and can range from 1,000,000 to 30,000,000 amu. The most common method to make flocculants is through a free-radical polymerization of vinyl-based monomers, of which acrylamide and acrylic acid are examples. Flocculants act to gather particles through charge interactions. As more particles gather on the polymer chain the size and weight of the particle mass increases. This causes the flocculated particles to separate out and causes solid-liquid separation.

All dosages of polymer recited in this patent application are given in terms of ppm of polymer as product. An example of the necessary calculation for determining polymer dose is:

Adding 2 grams of the neat polymer to 198 grams of water makes a 1% solution of the polymer of this invention. The mixture is stirred vigorously to activate the polymer. This solution is then dosed to 200 ml of the sluice. 1 ml of a 1% solution equals 50 ppm of polymer as product. See calculation below.

$$\frac{1 \text{ ml of } 1\% \text{ solution} \times 1 \times 10^6}{200 \text{ ml Sluice}} = 50 \text{ ppm (as product)}$$

The same methodology is employed for the field trials.

Sluice: The liquid component of wash water used on diatomaceous earth in a sugar manufacturing process.

RSV stands for Reduced Specific Viscosity, which is an indication of polymer chain length and average molecular weight. The RSV is measured at a given polymer concentration and temperature and calculated as follows:

$$RSV = \frac{[(\eta/\eta_o) - 1]}{c}$$

$\eta$ = viscosity of polymer solution $\eta_o$ = viscosity of solvent at the same temperature $c$ = concentration of polymer in solution.

In this patent application, the units of concentration "c" are (grams/100 ml or g/deciliter). Therefore, the units of RSV are dl/g. In this patent application, for measuring RSV, the solvent used was 1.0 N sodium nitrate solution. A 0.045% solution of the polymer was used. The RSV was measured at 30 ° C. The viscosities $\eta$ and $\eta_0$ were measured using a Cannon Ubbelohde semimicro dilution viscometer, size 75. The viscometer is mounted in a perfectly vertical position in a constant temperature bath adjusted to 30±0.02° C. The error inherent in the calculation of RSV is about 2 dl/grams. When two polymers of the same chemistry have similar RSVs that is an indication that they have similar molecular weights.

The first aspect of the invention is a flocculant dispersion polymer comprising:

a first monomer component, which is nonionic;

a second monomer component, which is cationic; and a third monomer component which is diallyl dimethylammonium chloride.

In this polymer, the second monomer component supplies the bulk of the cationic charge and in conjunction with the first monomer component, provides a high molecular weight. The third monomer component, DADMAC, is used for the detection. The third monomer component also provides some additional cationic charge to the polymer. The difficulty in creating this flocculant is that increasing the DADMAC concentration increases the sensitivity to the immunoassay but decreases the polymer's effectiveness as a flocculant due to loss of polymer molecular weight.

The first monomer component is selected from the group consisting of acrylamide, vinylacetate, vinylcaprolactam, protonated acrylamidopropylsulfonic acid, protonated 2-sulfoethylacrylate, substituted or non-substituted amides or esters of acrylic acid, including, but not limited to N,N-dimethylacrylamide, N-t-butylacrylamide, N-isopropyl acrylamide, hydroxymethylacrylate, hydroxyethylacrylate, hydroxypropylacrylate, hydroxybutylacrylate, substituted or non-substituted amides or esters of methacrylic acid, including, but not limited to N,N-dimethylmethacrylamide, N-methylmethacrylamide, N-isopropyl methacrylamide, hydroxymethylmethacrylate, hydroxyethylmethacrylate, hydroxypropylmethacrylate, and hydroxybutylmethacrylate.

The second monomer component is selected from the group consisting of:

dimethylaminoethylacrylate methyl chloride salt (DMAEA.MCQ);

dimethylaminoethylmethacrylate methyl chloride salt (DMAEM.MCQ);

dimethylaminoethylmethacrylate methyl sulfate salt (DMAEM.MSQ);

dimethylaminoethylmethacrylate benzyl chloride salt (DMAEM.BCQ);

dimethylaminoethylacrylate methyl sulfate salt (DMAEA.MSQ);

dimethylaminoethylacrylate benzyl chloride salt (DMAEA.BCQ), methacrylamidopropyl trimethylammonium chloride (MAPTAC);

acrylamidopropyl trimethylammonium chloride (APTAC);

2-vinylpyridine; and 4-vinylpyridine.

The third monomer component is diallyldiammonium chloride.

The first monomer component, which is nonionic, is present in an amount of from about 5 mole percent to about 80 mole percent of the total polymer. Preferably, it is present in an amount of from about 25 mole percent to about 75 mole percent, and most preferably, the first monomer component is present in an amount of about 60 mole percent of the total polymer.

The second monomer component, which is cationic, is present in an amount of from about 5 mole percent to about 90 mole percent of the total polymer. Preferably, it is present in an amount of from about 5 mole percent to about 50 mole percent, and most preferably, the second monomer component is present in an amount of about 30 mole percent of the total polymer.

The third monomer component, which is diallyldiammonium chloride, is present in an amount of from about 3 mole percent to about 30 mole percent of the total polymer. Preferably, it is present in an amount of from about 3 mole percent to about 20 mole percent, and most preferably, the third monomer component is present in an amount of about 10 mole percent of the total polymer.

When selecting the various mole percentage of each component it is important to note that the mole percentages must be selected such that all three monomer components are present in at least a minimum of 3 mole percent of the polymer. Thus, the possible range for mole percent of monomer components in this dispersion polymer is as follows:

from about 5 to about 80 mole percent of the first monomer component, which is nonionic;

from about 5 to about 90 mole percent of the second monomer component, which is cationic; and from about 3 to about 30 mole percent of the third monomer component, which is diallyldimethylammonium chloride.

The composition of the preferred polymer used for dewatering in the sugar food-processing application; is about 60 mole percent first monomer component which is acrylamide;

about 30 mole percent second monomer component which is dimethylaminoethylacrylate methyl chloride salt (DMAEA.MCQ);

and about 10 mole percent diallyldiammonium chloride.

The most preferred polymer(s) for use in other solid-liquid food processing applications or solid-liquid industrial applications will vary based on the charge demand of the material to be flocculated.

Owing to the sensitivity of the immunoassay and its affinity to diallyldimethylammonium chloride, it is doubtful that substantive changes in this molecule would be tolerated. Subtle changes like changing the counter ion from chloride to bromide or to methylsulfate or any other halogen or pseudohalogen should not effect the system. Other changes to the integrity of the DADMAC molecule, like substituting "diethyl" for dimethyl, will be detrimental in regards to the detectability of this polymer.

The polymers of the instant claimed "cationic flocculant dispersion polymer" composition of matter invention are made in a dispersion polymerization. It is possible to make them in a latex form, but it is understood that the latex versions of these polymers are known in the art and are not to be considered polymers of the instant claimed "cationic flocculent dispersion polymer" composition of matter invention, even though the latex versions of these polymers can be used in the instant claimed "method of flocculating solids" invention.

In addition to all the other differences enumerated below, an advantage of making the polymer in a dispersion form is that there are no polymerization oils present with the polymer. This is an advantage, because it is undesirable to have polymerization oils present in any food process streams.

It is also possible to make the cationic flocculant polymers in what is known in the art as a dry form. Methods to make these cationic flocculant polymers in a dry form are known to persons of ordinary skill in the art.

A batch or semi-batch polymerization method can be employed to prepare the dispersion polymer of the present invention. During a batch polymerization, the polymeric stabilizers, chain transfer agents, monomers, chelant, and water are initially added to the reactor. All or a portion of the formulation salt/salts are also added to the reactor at this time. Mechanical agitation is started and the reactor contents are heated to the desired polymerization temperature. When the set-point temperature is reached, the initiator is added and a nitrogen purge is started. The reaction is allowed to proceed at the desired temperature until completion and then the contents of the reactor are cooled. Additional inorganic salts may be added during or after the polymerization to maintain processability or influence final product quality. Moreover, additional initiator may be added during the reaction to achieve desired conversion rates and facilitate reaction completeness.

Use of a semi-batch polymerization method will vary from a batch polymerization method only in that one or more of the monomers used in the synthesis of the polymer are held out in part or whole at the beginning of the reaction. The withheld monomer is then added over the course of the polymerization. If acrylamide monomer is used as a semi-batch monomer, a chelant is often also added during the semi-batch period.

The dispersion polymers of the instant claimed invention include the three monomer components detailed above, namely an nonionic monomer component, a cationic monomer component, and a DADMAC monomer component. In addition, the dispersion polymer includes other reaction components of water, inorganic salts, polymeric stabilizers, chain transfer agents, initiators, and RSV stabilizers. The purpose of the water is to act as a polymerization media. Inorganic salts and polymeric stabilizers serve to promote precipitation and act as processing aids. The polymeric stabilizer also serves as a particle stabilizing agent. The chain transfer agent serves as a polymer molecular weight modifier. The initiators are used to initiate the polymerization reaction. The RSV stabilizers are used to stabilize the molecular weight of the polymer.

As briefly mentioned previously, unlike conventional latex polymers utilized in dewatering processes, the dispersion polymer of the instant claimed invention does not contain any oil or surfactant. The monomers, salts, and water are charged to a reaction vessel along with the polymeric stabilizers. As the reaction proceeds, polymer chains are formed and grow rapidly. Because these polymers are in a high ionic strength salt solution, they tend to coil upon themselves. As noted above, the polymeric stabilizers aid in the stabilization of these coiled polymers, which turn into dense polymer particles. To use the dispersion polymers, the polymer solution is added to water. The change in ionic strength allows the polymers to uncoil and expand. At this time, the dispersion polymers are ready for use.

Since the dispersion polymers do not contain surfactants or oil, the dispersion polymers are more environmentally friendly and more ideally suited for food applications, than the latex polymers. Moreover, the absence of oil in the dispersion polymers equates to such polymers having virtually zero volatile organic content (VOC), which is another environmental advantage of such polymers.

Still further, because the dispersion polymers are not emulsified in an oil matrix like latex products, but rather are aqueous solutions of suspended polymer in salt water, simple dilution of the dispersion products with water renders the polymer in a useful state. Moreover, not only is the simplicity of use an advantage of the dispersion polymers, the present invention provides cost savings to users since there is no need to purchase complicated and expensive polymer dilution/feed systems when using such dispersion polymers.

It has been surprisingly found that the third monomer component, which is diallyldimethylammonium chloride, affords the ability to detect the polymers of the present invention. The polymers are detectable with the use of hybridoma cell lines producing monoclonal antibodies having an affinity for the incorporated DADMAC monomer present in the polymer. Suitable immunoabsorbent assays for use in the present invention can be prepared accordingly to the procedures detailed in U.S. Pat. No. 5,593,850, the disclosure of which is incorporated herein by reference. They are also commercially available as the "Nalco®8103 (polyDADMAC) immunoassay test kit" sold by Nalco Chemical Company.

In U.S. Pat. No. 5,593,850, a method of detecting water-soluble polymers using monoclonal antibodies is taught. These antibodies were derived by injecting a polymer into a rabbit; the rabbit then generates antibodies to combat that specific foreign body. The antibody producing cells are harvested from the rabbit and cultured to produce useful amounts of the antibodies. Examples of polymers that can be detected using this technique include Nalco®8103, Nalco®8105 and Prism®polymers, which are all available from Nalco Chemical Company. All of these polymers were injected into animals, which formed the specific antibody. An antibody can be viewed as the lock and the antigen (the polymer) as the key, with the understanding that only that one special key will fit into each specific lock.

A different technique was used with the polymers synthesized in this work. In this work, a polymer was synthesized. The polymer was not injected into a rabbit, nor were specific antibodies generated from it. The polymer created contains a specific amount of incorporated DADMAC monomer, which is the same monomer used to make Nalco®8103, which is capable of being detected using the immunoassay method of U.S. Pat. No. 5,593,850. In this work, it has been found that the antibody for DADMAC polymer will identify the whole polymer by focusing on the incorporated DADMAC monomer components of the polymer. It was quite unexpected that the use of an antibody that is selective for polyDADMAC would also work to detect a polymer that has other monomers in it with only a very small amount of DADMAC being one of the monomers present. The reason this is unexpected is that it was uncertain whether the antibody would "recognize" the incorporated DADMAC moiety while in this more complicated matrix. However, it has been found that the flocculant polymers of the present invention can be measured down to ppb levels using the immunoassay method of U.S. Pat. No. 5,593,850.

In actual practice, the concentration of cationic polymer is determined by immunoassay. First, the sample of water is incubated with a monoclonal antibody having an affinity for the diallyldimethylammonium chloride (DADMAC) moiety, which acts as an antigen in the cationic flocculant polymer. The affinity is strong enough to recognize a cationic flocculant polymer containing the DADMAC moiety and to differentiate the cationic flocculant polymer from other polymers in the water sample. Next, the immunoassay involves measuring the degree of binding of the monoclonal antibody with the DADMAC moiety. The concentration of the cationic flocculant polymer is then determined based on the degree of binding of the monoclonal antibody see *Analusis,* 25(7), 25–29 (1997).

In a preferred embodiment, the degree of antibody binding is determined by a "sandwich" enzyme linked immunosorbent assay (hereinafter "ELISA"). In this assay, the antibodies are conjugated to both magnetic particles and an enzyme. When the conjugated antibodies are incubated with a water sample containing the polymer, the antibodies recognize and bind with the DADMAC moiety antigen on the polymer. The resulting complex is a "sandwich" of enzyme-antibody-antigen-antibody-magnetic particle. This sandwich is then separated from the rest of the water sample by exposure to a magnet. The sandwich is fixed to the magnet, and the remaining sample is decanted and rinsed away. The sandwich is then removed from the magnet and then it is re-suspended in a solution of a substrate of the enzyme in the sandwich. The enzyme in the sandwich catalyzes the reaction of the substrate to some detectable compound. An example of this reaction is the dephosphorylation of p-nitrophenyl phosphate to yield p-nitrophenol. The p-nitrophenol is yellow in color. The increase in yellow color is proportional to the enzyme-sandwich concentration which, in turn, is proportional to the polymer concentration.

Thus, the concentration of the cationic flocculant polymer is determined using these antibody techniques. Knowing the concentration of the cationic flocculant polymer is of great value for industrial food processes wherein system requirements dictate that the amount of flocculant polymer present, after the solid-liquid system has been flocculated, must be known. Using the immunoassay methods described herein, cationic flocculant polymers of the present invention, and their latex counterparts can be detected down to parts per billion ("ppb") levels. It has been found in practice that the dispersion cationic flocculant polymers of the instant claimed invention can be detected down to 50 ppb.

Significant advantages are obtained as a result of such detection sensitivity. For instance, the supernatant in a liquid sample can now be tested pursuant to the present invention to quantify the amount of flocculant polymer contained therein. This allows the determination to be made as to whether certain effluent should or should not be discarded based on the quantity of flocculant polymer present. An example of this is whether liquid containing sugar should be discarded, in an environmentally safe manner, or further attempts made to recover the sugar. In the past the liquid would have been discarded due to concerns about possible contamination with flocculant polymer. Now, using the polymers and methods of the instant claimed invention it will be possible to detect exactly how much cationic flocculant polymer is present in the liquid and thus it will be possible to recover sugar from liquid with quantifiable amounts of polymeric flocculant present.

The second aspect of this invention is a method of flocculating solids from the liquid component of an industrial food process, the method comprising the steps of:
  a) adding a cationic flocculant polymer to a liquid component of an industrial process which causes the formation of flocculated particles, wherein said cationic flocculant polymer comprises a first monomer component, which is nonionic;
  a second monomer component, which is cationic; and
  a third monomer component which is diallyl dimethylammonium chloride;
  wherein the first monomer component, which is nonionic, is selected from the group consisting of:
  acrylamide, vinylacetate, vinylcaprolactam, protonated acrylamidopropylsulfonic acid, protonated 2-sulfoethylacrylate, substituted or non-substituted amides or esters of acrylic acid, including, but not limited to: N,N-dimethylacrylamide, N-t-butylacrylamide, N-isopropyl acrylamide, hydroxymethylacrylate, hydroxyethylacrylate, hydroxypropylacrylate, and hydroxybutylacrylate, substituted or non-substituted amides or esters of methacrylic acid, including, but not limited to: N,N-dimethylmethacrylamide, N-methylmethacrylamide, N-isopropyl methacrylamide, hydroxymethylmethacrylate, hydroxyethylmethacrylate, hydroxypropylmethacrylate, and hydroxybutylmethacrylate;
  wherein the second monomer component, which is cationic, is selected from the group consisting of: dimethylaminoethylacrylate methyl chloride salt (DMAEA.MCQ); dimethylaminoethylmethacrylate methyl chloride salt (DMAEM.MCQ); dimethylaminoethylmethacrylate methyl sulfate salt (DMAEM.MSQ); dimethylaminoethylmethacrylate benzyl chloride salt (DMAEM.BCQ); dimethylaminoethylacrylate methyl sulfate salt (DMAEA.MSQ); dimethylaminoethylacrylate benzyl chloride salt (DMAEA.BCQ), methacrylamidopropyl trimethylammonium chloride (MAPTAC); acrylamidopropyl trimethylammonium chloride (APTAC); 2-vinylpyridine; and 4-vinylpyridine;
  b) separating said flocculated particles from said liquid component; and
  c) determining the concentration of said cationic flocculant polymer in the liquid; wherein the step of determining the concentration of the cationic flocculant polymer further comprises:
    i) incubating the sample of liquid with a monoclonal antibody having an affinity for the cationic flocculant polymer, the affinity being strong enough to recognize a monomer antigen in the cationic flocculant polymer and to differentiate the cationic flocculant polymer from other polymers in the sample;
    ii) detecting and measuring the degree of binding of the monoclonal antibody with the monomer antigen; and
    iii) determining the concentration of the cationic flocculant polymer based on the degree of binding of the monoclonal antibody.

The industrial food processes wherein the method of the instant claimed invention can be practiced include processes in the sugar manufacturing industry.

The refinement of sugar, either from cane or sugar beets, is a multi-step process which eventually leads to table sugar (sucrose). As the crops arrive at the mills, they contain soil and trash accumulated during the harvesting operation. In the case of cane sugar harvested by pushers, similar to bulldozers, the refuse may constitute as much as 10% to 25% of the weight of the material delivered to the mill. Because of this, purification is a critical operation to the preparation of raw materials going to further extraction processes.

After a thorough washing of the cane or sugar beets, sucrose is extracted from the raw material. In cane sugar mills, this is usually done by crushing and milling the washed, cut cane stocks, producing a juice containing approximately 12% to 15% sucrose. Whereas, with sugar beets, the beets are sliced into long, narrow pieces (cossettes) and the sucrose extracted by washing with water in diffusers at about 160° F.

The cane stocks are pressed after initial crushing and milling to reclaim as much sugar as possible, and the remaining solids (bagasse) are usually burned in boilers to generate steam. Bagasse may also be used as a raw material for such products as insulation board or acoustical tile. In the beet sugar industry, the beet pulp residue is quite high in protein, and it may be mixed with some of the plant production of molasses for cattle feed.

The crystallization step utilized in desugarization processes is the main driving force in purifying sugar. Sugar crystals from the mother liquor are removed and successively recrystallized. The "impurities" of these successive recrystallizations are concentrated into a thick solution known as molasses.

Molasses contains approximately 50% sucrose and other nitrogenous compounds such as betaine, invert sugar, organic acids such as glutamic acid, and other compounds that come from the sugar cane or beet. Because of its high sugar and nitrogenous content, molasses is a valuable raw material used in the fermentation industry. It is also used in animal feed supplements and by the pharmaceutical industry. Indeed, molasses sales are an additional source of revenues for sugar producers.

Since molasses is roughly 50% sugar, some sugar manufacturers also see it as an additional source of sugar that can be re-refined. A known process for the extraction of sugar from molasses involves a multi-stage ion exchange column. The effluent resulting from this process, which contains sugar, is then mixed with diatomaceous earth and is sent to a plate and frame press for dewatering. The dissolved sugar is in the effluent and is sent for further refinement at the head of a plant. However, a significant portion of the sugar that has absorbed onto the diatomaceous earth still exists as absorbed onto the earth.

Therefore, after pressing, the diatomaceous earth is re-slurried with water. This allows for any absorbed sugar to re-dissolve and increase the yield of reclaimed sugar. At this point, conventional processes have attempted to add a traditional flocculant polymer to flocculate the diatomaceous earth. The settled solids, containing sugar flocculated out of the liquid, are then sent for further dewatering using a pneumatic press.

Theoretically, the supernatant, which still contains residual sugar, can be further refined. However, because of the addition of a flocculant polymer, questions exist as to whether the effluent is contaminated with such polymer. This contamination limits the use of the effluent and therefore significantly cuts into the overall yield of the recoverable sugar.

The present invention provides methods and compositions that allow for the detection of a flocculant in a treatment system. The dispersion polymers of the present "cationic flocculant dispersion polymer" composition of matter invention as well as their latex polymer and dry polymer cognates are flocculants that possess a high cationic charge and sufficient molecular weight to effect adequate solid-liquid separation. Such polymers produce a strong floc that can withstand the pressure associated with dewatering. Still further, both the dispersion polymers of the present "cationic flocculant dispersion polymer" composition of matter invention as well as their latex polymer and dry polymer cognates can be detected using an enzyme linked immunosorbent assay; the detection sensitivity being in the parts per billion range.

In addition to molasses processing, the present invention can also be utilized to increase the sugar yield from standard liquor. Standard liquor processing is the recovery of sugar from thickened beet juice. It is a cleaner process than molasses recovery, but still requires pre-purification before it can enter the crystallization pans. As in the molasses process, the standard liquor is mixed with diatomaceous earth and then filtered through a plate and frame press.

Again, there is a significant absorption of sugar onto the diatomaceous earth. To collect this sugar, the diatomaceous earth is reslurried with water and sent to a settling tank. At this time, the cationic flocculant polymer of the present invention is added to the settling tank. This polymer flocculates the diatomaceous earth and allows for effective solid/liquid separation. The decant, which contains sugar, is then sent for further processing and the solid is sent for dewatering. Again, the pressed effluent from the dewatering also has a high sugar concentration and is taken for further processing as well.

Pursuant to the present invention, the cationic flocculant polymer is added to the settling tank in an amount effective to promote solid/liquid separation. Specifically, the cationic flocculant polymer is added in an amount of about 200 ppm to about 2000 ppm. Preferably, about 400 ppm to about 1000 ppm of cationic flocculant polymer is utilized in the methods of the present invention. Most preferably about 600 ppm to about 700 ppm of cationic flocculant polymer is utilized in the method of the present invention.

Essentially, the traceable flocculant of the present invention can be used in any system where a flocculant is used and where determining the concentration of such flocculant in the treatment process would be beneficial. It is especially beneficial in food processing where polymer contamination is not tolerable. For example, the present invention can be utilized in sugar refinery systems to dewater molasses and standard liquor sluices and in juice clarification systems.

The following examples are intended to be illustrative of the present invention and to teach one of ordinary skill how to make and use the invention. These examples are not intended to limit the invention or its protection in any way.

EXAMPLES

Throughout these examples these descriptions apply to the indicated polymers.

| Name | Polymer Type | Polymer Mole % Composition AcAm/DMAEA.MCQ/ DADMAC | % Actives | RSV (dl/g) |
|---|---|---|---|---|
| Polymer A | Latex | 60/30/10 | 30 | 20 |
| Polymer B | Dispersion | 60/30/10 | 20.5 | 9.7 |
| Polymer C | Dispersion | 60/30/10 | 20.2 | 10.3 |
| Polymer D | Latex | 60/30/10 | 30 | 10.0 |
| Polymer E | Latex | 66/34 AcAm/ DMAEM.MCQ | 35 | 15 |

Polymers A, D and E are not cationic flocculant dispersion polymers of the instant claimed composition of matter invention; although Polymer A and Polymer D (along with Polymer B and Polymer C) can be used in the instant claimed "method of flocculating solids" invention. Polymer E cannot be used in the instant claimed "method of flocculating solids" invention; it is included here as a comparative example.

Example 1

Dispersion Polymerization of a 20.5% Polymer Solids Acrylamide/Dimethylaminoethyl Acrylate Methyl Chloride Quaternary Salt/Diallyldimethyl Ammonium Chloride using Semi-Batch Technique A 20.5% polymer solids, 60/30/10 mole percent acrylamide/dimethylaminoethyl acrylate methyl chloride quaternary salt/diallyldimethyl ammonium chloride dispersion polymer was synthesized in the following manner. A 1500 cc reaction flask was fitted with a mechanical stirrer, thermocouple, condenser, nitrogen purge tube, an addition port fitted with tubing attached to a syringe pump, and heating tape. To this reaction flask was added 80.3 g of acrylamide (50% aqueous solution, available from Nalco Chemical Company), 34.2 g of dimethylaminoethyl acrylate methyl chloride quaternary salt (80% aqueous solution available from CPS Chemical Company of Old Bridge, N.Y.), 44.6 g of diallyldimethyl ammonium chloride (62% aqueous solution, available from Nalco Chemical Company), 60.0 g of a homopolymer of dimethylaminoethyl acrylate chloride quaternary (15% aqueous solution, available from Nalco Chemical Company), 45.5 g of homopolymer of diallyldimethylammonium chloride (15% aqueous solution, available from Nalco Chemical Company), 12.0 g of polyethylene glycol (molecular weight 400, available from Aldrich Chemical Co. of Milwaukee, Wis. (1-800-558-

9160)), 0.2 g of ethylenediaminetetraacetic acid, tetra sodium salt (available from Dow Chemical Company of Midland, Mich. ((517) 636-1000)), 190.0 g of ammonium sulfate, 50.0 g sodium sulfate, and 302.9 g of deionized water.

The mixture was heated to 48° C., 2.0 g of a 1.0% aqueous solution of 2,2'-azobis(2-amidinopropane) dihydrochloride (Wako VA-50), available from Wako Chemicals of Dallas, Tex.) was added to the reaction mixture and a constant purge of nitrogen was started. The temperature was maintained at 48° C. for one hour and then a semi-batch feed of a monomer solution was started. The feed consisted of a mixture of 65.7 g of acrylamide (50% aqueous solution), 90.1 g of dimethylaminoethyl acrylate methyl chloride quaternary salt (80% aqueous solution), and 0.1 g of ethylenediaminetetraacetic acid, tetra sodium salt. The monomer mixture was fed in over approximately 4 to 4½ hours. A two stage monomer addition rate was used with approximately ⅔ of the monomer solution being fed into the reaction during the first ½ of the feed period and the remaining ⅓ of the monomer solution being fed in during the last ½ of the feed period. One hour after the semi-batch monomer solution feed addition was complete, a solution of 0.4 g of 2,2'-azobis(2-amidinopropane) dihydrochloride in 2.0 g deionized water was added to the reaction and the temperature was maintained at 48° C. for an additional hour before cooling.

The final product was a smooth creamy white dispersion with a bulk viscosity of 870 cp. Upon dilution to a 0.5% solution of polymer in 2% aqueous ammonium sulfate, a solution viscosity measurement of 34 cp. was obtained. A reduced specific viscosity of 9.7 dl/g was measured for a 0.045% solution of the polymer in 1.0N sodium nitrate at 30° C.

In the following examples this is Polymer B.

Example 2

Dispersion Polymerization of a 20.2% polymer Solids Acrylamide/Dimethylaminoethyl Acrylate Methyl Chloride Quaternary Salt/Diallyldimethyl Ammonium Chloride using Semi-Batch Technique A 20.2% polymer solids, 60/30/10 mole percent acrylamide/dimethylaminoethyl acrylate methyl chloride quaternary salt/diallyldimethyl ammonium chloride dispersion polymer was synthesized in a method similar to that described in Example 1. To the reactor setup described above was added 22.4 g of acrylamide (48.9% aqueous solution), 18.6 g of dimethylaminoethyl acrylate methyl chloride quaternary salt (80% aqueous solution), 44.3 g of diallyldimethyl ammonium chloride (62.4% aqueous solution), 60.0 g of a homopolymer of dimethylaminoethyl acrylate methyl chloride quaternary (15% aqueous solution, available from Nalco Chemical Company), 45 g of a homopolymer of diallyldimethyl ammonium chloride (15% aqueous solution), 12.0 g of polyethylene glycol (mw. 400), 0.1 g of ethylenediaminetetraacetic acid, tetra sodium salt, 190.0 g of ammonium sulfate, 50.0 g sodium sulfate, and 300.0 g of deionized water.

The mixture was heated to 48° C. while stirring at 900 rpm. After reaching 48° C., 2.0 g of a 1.0% aqueous solution of 2,2'-azobis(2-amidinopropane) dihydrochloride was added to the reaction mixture and a constant purge of nitrogen was started. The temperature was maintained at 48° C. for one hour and then a semi-batch feed of a monomer solution was started. The feed consisted of a mixture of 126.9 g of acrylamide (48.9% aqueous solution), 105.6 g of dimethylaminoethyl acrylate methyl chloride quaternary salt (80% aqueous solution), and 0.15 g of ethylenediaminetetraacetic acid, tetra sodium salt. The monomer mixture was fed in over approximately 4 to 4½ hours and the same two stage monomer addition rate described in Example No. 1 was employed. At 4.5 hours, the agitation was increased to 1000 rpm. At 5.5 hours, 10 g sodium sulfate was added. At 6.25 hours, a solution of 0.4 g of 2,2'-azobis(2-amidinopropane) dihydrochloride in 2.0 g deionized water was added to the reaction and the temperature was maintained at 48° C. for an additional hour before cooling.

The final product was a smooth creamy white dispersion with a bulk viscosity of 700 cp. A reduced specific viscosity of 10.3 dl/g was measured for a 0.045% solution of the polymer in 1.0N sodium nitrate at 30° C.

In the following Examples, this is Polymer C.

Example 3

Effectiveness and Detectability of a Cationic Flocculant Polymer

Specifically, as indicated below, three flocculant polymers (one latex polymer and two dispersion polymers) were tested to determine if such flocculants would produce strong, dewaterable flocs and if the polymer could be detected with the sugar matrix according to the detection method disclosed herein.

Free drainage testing was conducted by placing 200 ml of the sluice into a 500 ml graduated cylinder, then adding the appropriate amount of the polymer solution. Dilution water was not needed in this application. The cylinder was then inverted to thoroughly mix the polymer and the sludge. The flocculated sludge was then poured over belt fabric and the drainage recorded at 5, 10 and 15 second intervals. The clarity of the filtrate and the quality of the cake was also recorded. In this particular test, a sample of the effluent was removed and a total suspended solids (hereinafter "TSS") analysis performed.

It was common in this investigation to dose the sluice at ppm levels, invert, pour over the filter fabric, and collect the filtrate for immunoassay analysis. Free drainage data for the first tested cationic flocculant polymer—Polymer A—is contained in Table I below.

Excellent floc formation was observed using Polymer A; the flocs were strong and had excellent water release. The flocculated solids did not bind to the press fabric and showed greater than 85% suspended solids capture.

TABLE I

| Dosage (ppm) | TSS ($\times 10^3$)(mg/l) | Free Drainage (ml) |
| --- | --- | --- |
| 0 | 50 | 110 |
| 500 | 8.5 | 168 |
| 550 | 7 | 176 |
| 600 | 7.5 | 176 |
| 800 | 8 | 180 |
| 1000 | 7.75 | 164 |
| 1500 | 4.3 | 158 |

Also tested were two dispersion polymers having the same monomer composition as Polymer A; these dispersion polymers are labeled as Polymer B and Polymer C. The waste effluent was low in solids, due to mechanical problems in the plant, but was tested anyway. Free drainage data is contained in Table II. Good floc formation and drainage was observed using these polymers. The cake was easily pressed and showed greater than 95% solids capture.

TABLE II

| Dosage (ppm) | Free Drainage Polymer B (ml) | Free Drainage Polymer C (ml) | TSS (mg/l) Polymer B | TSS (mg/l) Polymer C |
|---|---|---|---|---|
| 0 | 110 | 110 | 5250 | 5250 |
| 200 | 130 | 138 | 275 | 150 |
| 400 | 148 | 154 | 175 | 250 |
| 600 | 154 | 166 | 275 | 200 |

Example 4

In addition to testing whether the experimental flocculants of the present invention could form strong flocs, the ability to detect the polymers pursuant to the detection method of the present invention was also investigated. The detection method utilizes an immunoassay that detects the flocculant polymer using antibodies. These antibodies specifically bind to selective points on the polymer backbone. Additionally, these antibodies are tagged with iron molecules, to help separate and purify the polymer-antibody complex.

The immunoassay kit used in the experimental investigation was originally developed for the detection of polyDADMAC. The immunoassay kit was obtained from Nalco Chemical Company of Naperville, Ill. Polymer A has incorporated DADMAC monomer, at a low (10 mole %) concentration. Laboratory studies have shown this polymer to be responsive to the antibodies in this assay. Because the tested polymer is significantly different than polyDADMAC, a standard curve was generated. To get the standard curve, Polymer A was diluted to 100, 300, 600 and 1000 ppb (based on product). These standards are usually run in duplicate and absorbances averaged. A "best fit" line was then generated, and its formula used for polymer detection in the actual application. Testing was conducted over a 4-day period.

Example 4A

The first set of detection tests for the Polymer A polymer are contained in Table III below. First, the standard curve was run. The waste effluent was molasses sluice (as opposed to standard liquor sluice) and was treated with 200, 400, 500 and 600 ppm of Polymer A. The solids were filtered and a portion of the effluent saved for polymer analysis, The effluent was prepared by placing a 1 ml aliquot of the sample in the standard sat buffer solution, available from the commercial assay kit, then adding 1 ml of the buffer solution to the tube containing the antibody. After washing and development, the tube was placed in a spectrometer and its absorbance measured.

TABLE III

| Dosage (ppb) | Absorbance |
|---|---|
| 100 | 0.372 |
| 300 | 0.997 |
| 600 | 1.519 |
| 1000 | 1.793 |

Tabular data for testing on molasses sluice is contained in Table IV below. A standard on the sluice was run so that any extraneous values could be subtracted from the final absorbance. At 200 ppb of Polymer A, a negative value of polymer was calculated. This was interpreted as an undetectable amount of polymer. The calculated concentration rises with increasing dosage, as would be expected in an overdose situation.

TABLE IV

| Molasses Sluice (bench) Polymer A Dose (ppm) | Abs | Calculated Concentration (ppb) |
|---|---|---|
| 400 | 0.694 | 94.5 |
| 500 | 1.714 | 774.5 |
| 600 | 2.12 | 1045.2 |
| Blank | 0.145 | |

Two dispersion polymers, Polymer B and Polymer C, having the same monomer composition as Polymer A were then tested on molasses sluice. Again, standard curves were established for each of these polymers. See Table V below. The sluice was dosed with 200, 400 and 600 ppm of the dispersion polymers. The effluents were collected and tested for residual polymer. Like Polymer A, these polymers gave a positive interaction with the antibodies and calculation of polymer concentration in the effluent was possible (see Table VI below).

TABLE V

| | Absorbance |
|---|---|
| STANDARD Polymer B (ppb) | |
| 100 | 0.309 |
| 300 | 0.42 |
| 600 | 1.141 |
| 1000 | 1.888 |
| STANDARD Polymer C (ppb) | |
| 100 | 0.091 |
| 300 | 0.442 |
| 600 | 1.085 |
| 1000 | 1.114 |

TABLE VI

| | Absorbance | Calculated Concentration (ppb) |
|---|---|---|
| Molasses Sluice Polymer B Dosage (ppm) | | |
| 200 | 0.383 | 123.9 |
| 400 | 1.078 | 510.0 |
| 600 | 1.555 | 775.0 |
| Molasses Sluice Polymer C Dosage (ppm) | | |
| 200 | 0.494 | 211.7 |
| 400 | 1.48 | 1033.3 |
| 600 | 1.698 | 1215.0 |
| Blank | 0.145 | |

Example 4B

Ten gallons of Polymer A were made to test at an on-site evaluation at a sugar refinery plant. Currently, the plant dewaters respective sluices with Polymer E Moreover, the plant makes up its polymer as a 1.5% solution in a 450-gallon batch of product solution. Not wanting to significantly alter this methodology, a 1.5% solution of Polymer A was made. Polymer A has less polymer actives than Polymer E (30 vs. 35%), so a more dilute polymer solution will be made.

Trial data is represented in Table VII below, using standard liquor sluice. The initial TSS was greater than 50,000 ppm. Batch #1 was a 98/2 mixture of Polymer A and Polymer E. The material pressed well, formed a good solid cake, and captured greater than 90% of the suspended solids. Immunoassay on the effluent showed a residual polymer content of 148 ppb. The second run, like the first, showed excellent cake formation and pressability. Solids capture was greater than 90% and the effluent had a residual polymer concentration of 192 ppb. On the third and final batch, an operator inadvertently added water to the polymer solution. Whatever polymer was left was added and the resulting solution concentration was about 1.2%. Dewatering proceeded normally; in fact, it was better than the previous runs. The cake was drier and stood taller on the fabric. The effluent TSS was reduced to greater than 92%, and the residual polymer in the effluent was reduced to below 50 ppb.

The test results demonstrate that excellent floc formation, free drainage, solids capture and pressability was observed in both bench and pneumatic press testing. The experimental polymers (including the latex as well as the dispersion polymers) were effective flocculants for both the standard liquor and the molasses sluice. In addition, polymers with the composition of the present invention could be detected, at ppb levels, in the bench test supernatant and press effluents.

TABLE VII

| Field Trial of Polymer A | | Calc. Conc. | Poly. Conc. Feed | TSS |
|---|---|---|---|---|
| Dosage | Abs | (ppb) | to Batch Tank | (mg/l) |
| Pressate 1*@560 ppm | 0.547 | 147.8 | 1.50% | 4600 |
| Pressate 2 @560 ppm | 0.627 | 192.2 | 1.50% | 4500 |
| Pressate 3 @475 ppm | 0.303 | <50 | 1.20% | 4000 |
| *(98/2 mixture) | | | | |
| Batch size = 3875 gallons | | | | |

Example 5

An additional field evaluation was conducted at the same Northwestern sugar processor as described in Example 4B. Testing was done to determine the effectiveness of the polymer treatment over a variety of different conditions and using different streams (molasses or beet juice). In addition, a new test variable was added, which was the concentration of Polymer A in the press effluent (pressate). Press effluent is the liquid squeezed out, from the mechanical dewatering. The set-up was the same as Example 4B. Table VIII contains the results from the extended field trial. Since floc and cake formation were no longer in question, work focused on the residual polymer determination in both the decant and the pressate.

TABLE VIII

Extended Field Evaluation of Polymer D

| Sample# | Polymer D Dosage (ppm) | Residual Polymer D in Decant (ppb) | Residual Polymer D in Press Effluent (ppb) |
|---|---|---|---|
| 1 | 970 | 441 | — |
| 2 | 970 | — | 129 |
| 3 | 970 | — | 216 |
| 4 | 970 | — | <50 |
| 5 | 970 | — | <50 |
| 6 | 1240 | 509 | — |
| 7 | 1240 | — | <50 |
| 8 | 1240 | — | <50 |
| 9 | 1240 | — | <50 |
| 10 | 850 | 51 | — |
| 11 | 850 | — | <50 |
| 12 | 850 | — | <50 |
| 13 | 850 | — | <50 |
| 14 | 850 | — | <50 |
| 15 | 900 | 66 | — |
| 16 | 900 | — | <50 |
| 17 | 900 | — | 256 |
| 18 | 900 | — | <50 |

There is some wide variability in the residual polymer data, which can easily be explained. The variability comes from sampling. Sampling early in the settling stage or before settling begins, affords a sample that is high in solids and therefore high in polymer (which is attached to the solids). Sampling later in the settling period should show a lower amount of solids and a truer value of residual polymer in the effluent. This idea was tested and is shown in Table IX.

TABLE IX

Polymer Concentration vs. Clarification Settling Time

| Settling Time (min) | Residual Polymer D in Decant (ppb) |
|---|---|
| 0 | 1285 |
| 4 | 336 |
| 8 | <50 |
| 12 | <50 |
| 16 | <50 |
| 20 | <50 |
| final | <50 |

The same argument can be advanced for residual polymer in the pressate. Early in the pressing stage the diatomaceous earth is deposited onto the fabric and is pressurized. It is logical to assume that some polymer may be forced through the fabric during these earlier stages. Later in the process, after many depositions, the press effluent must percolate through the filter pad, thus giving a cleaner, more polymer free effluent. Testing was repeated multiple times to consume almost 700 gallons of Polymer D.

The significance of the single and extended trials show that Polymer D is
  i) effective in producing good solid/liquid separation (clarification and settling),
  ii) forms robust flocs that can withstand the shearing forces of mechanical dewatering (dewatering), and
  iii) that residual Polymer A can be detected and quantified in both the decant and the pressure effluents (detection).

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

We claim:

1. A cationic flocculant dispersion polymer comprising:
a first monomer component, which is nonionic;
a second monomer component, which is cationic; and
a third monomer component which is diallyl dimethylammonium chloride;
wherein the first monomer component, which is nonionic, is selected from the group consisting of: acrylamide, vinylacetate, vinylcaprolactam, protonanted acrylamidopropylsulfonic acid, protonated 2-sulfoethylacrylate; substituted or non-substituted amides or esters of acrylic acid, including, but not limited to: N,N,-dimethylacrylamide, N-t-butylacrylamide, N-isopropyl acrylamide, hydroxymethylacrylate, hydroxyethylacrylate, hydroxypropylacrylate, and hydroxybutylacrylate; substituted or non-substituted amides or esters of methacrylic acid, including, but not limited to: N,N-dimethylmethacrylamide, N-methylmethacrylamide, N-isopropyl methacrylamide, hydroxymethylmethacrylate, hydroxyethylmethacrylate, hydroxypropylmethacrylate, and hydroxybutylmethacrylate;
wherein the second monomer component, which is cationic, is selected from the group consisting of dimethylaminoethylacrylate methyl chloride salt; dimethylaminoethylmethacrylate methyl chloride salt; dimethylaminoethylmethacrylate methyl sulfate salt; dimethylaminoethylmethacrylate benzyl chloride salt; dimethylaminoethylacrylate methyl sulfate salt; dimethylaminoethylacrylate benzyl chloride salt, methacrylamidopropyl trimethylammonium chloride; acrylamidopropyl trimethylammonium chloride; 2-vinylpyridine; and 4-vinylpyridine.

2. The cationic flocculant dispersion polymer of claim 1 wherein the first monomer component is acrylamide and the second monomer component is dimethylaminoethylacrylate methyl chloride salt.

3. The cationic flocculant dispersion polymer of claim 1, wherein the ratio of monomer components is as follows:
from about 5 to about 80 mole percent of the first monomer component, which is nonionic;
from about 5 to about 90 mole percent of the second monomer component, which is cationic;
from about 3 to about 30 mole percent of the third monomer component, which is diallyl dimethylammonium chloride.

4. The cationic flocculant dispersion polymer of claim 1, wherein the ratio of monomer components is:
about 60 mole percent of the first monomer component,
about 30 mole percent of the second monomer component,
about 10 mole percent of the third monomer component.

5. The cationic flocculant dispersion polymer of claim 4, wherein said first monomer component is acrylamide, said second monomer component is dimethylaminoethylacrylate methyl chloride salt and said third monomer component is diallyl dimethylammonium chloride.

6. A method of flocculating solids from the liquid component of an industrial food process, the method comprising the steps of:
a) adding a cationic flocculant polymer to a liquid component of an industrial food process which causes the formation of flocculated particles, wherein said cationic flocculent polymer comprises a first monomer component, which is nonionic;
a second monomer component, which is cationic; and
a third monomer component which is diallyl dimethylammonium chloride;
wherein the first monomer component, which is nonionic, is selected from the group consisting of: acrylamide, vinylacetate, vinylcaprolactam, protonated acrylamidopropylsulfonic acid, protonated 2-sulfoethylacrylate; substituted or non-substituted amides or esters of acrylic acid, including, but not limited to: N,N,-dimethylacrylamide, N-t-butylacrylamide, N-isopropyl acrylamide, hydroxymethylacrylate, hydroxyethylacrylate, hydroxypropylacrylate, and hydroxybutylacrylate; substituted or non-substituted amides or esters of methacrylic acid, including, but not limited to: N,N-dimethylmethacrylamide, N-methylmethacrylamide, N-isopropyl methacrylamide, hydroxymethylmethacrylate, hydroxyethylmethacrylate, hydroxypropylmethacrylate, and hydroxybutylmethacrylate;
wherein the second monomer component, which is cationic, is selected from the group consisting of: dimethylaminoethylacrylate methyl chloride salt; dimethylaminoethylmethacrylate methyl chloride salt; dimethylaminoethylmethacrylate methyl sulfate salt; dimethylaminoethylmethacrylate benzyl chloride salt; dimethylaminoethylacrylate methyl sulfate salt; dimethylaminoethylacrylate benzyl chloride salt, methacrylamidopropyl trimethylammonium chloride; acrylamidopropyl trimethylammonium chloride;
b) separating said flocculated particles from said liquid component; and
c) determining the concentration of said cationic flocculant polymer in the liquid;
wherein the step of determining the concentration of the cationic flocculant polymer further comprises:
i) incubating the sample of liquid with a monoclonal antibody having an affinity for the cationic flocculant polymer, the affinity being strong enough to recognize a monomer antigen in the cationic flocculant polymer and to differentiate the cationic flocculant polymer from other polymers in the sample;
ii) detecting and measuring the degree of binding of the monoclonal antibody with the monomer antigen; and
iii) determining the concentration of the cationic flocculant polymer based on the degree of binding of the monoclonal antibody.

7. The method of claim 6 wherein said cationic flocculent polymer comprises:
a first monomer component, which is acrylamide;
a second monomer component, which is dimethylaminoethylacrylate methyl chloride salt; and
a third monomer component which is diallyl dimethylammonium chloride.

8. The method of claim 6 wherein said monomer antigen moiety is diallyl dimethylammonium chloride.

9. The method of claim 6 wherein the antigen-antibody binding is detected and measured by an enzyme-linked immunosorbent assay.

10. The method of claim 6 wherein said industrial food process is a sugar process.

11. The method of claim 10 wherein said sugar process is a molasses desugarization process.

12. The method of claim 10 where said sugar process is a beet juice process.

13. The method of claim 6 wherein said cationic flocculant polymer is a cationic dispersion flocculant polymer.

14. The method of claim 6 wherein said cationic flocculant polymer is a cationic latex flocculant polymer.

15. The method of claim 6 wherein said cationic flocculant polymer is a cationic dry flocculant polymer.

* * * * *